US00PP37176P2

(12) United States Plant Patent
Capo

(10) Patent No.: US PP37,176 P2
(45) Date of Patent: Dec. 23, 2025

(54) ***PETUNIA* PLANT NAMED 'KLEPH24827'**

(50) Latin Name: ***Petunia* x *atkinsiana* (syn. *P.* x *hybrida*)**
Varietal Denomination: KLEPH24827

(71) Applicant: KLEMM + SOHN GMBH & CO. KG., Stuttgart (DE)

(72) Inventor: Antonella Capo, Latina (IT)

(73) Assignee: Klemm + Sohn GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/268,767

(22) Filed: Jul. 14, 2025

(51) Int. Cl.
*A01H 6/82* (2018.01)
*A01H 5/02* (2018.01)

(52) U.S. Cl.
USPC ..... Plt./356.13

(58) Field of Classification Search
USPC ..... Plt./356.13
CPC ..... A01H 6/824; A01H 5/02
See application file for complete search history.

*Primary Examiner* — Keith O. Robinson
(74) *Attorney, Agent, or Firm* — Weatherly IP Solutions, LLC; Karen P. Bechtold; James Weatherly

(57) ABSTRACT

A new petunia plant particularly distinguished by pink-purple flowers with purple veins and a semi-trailing to trailing plant habit, is disclosed.

1 Drawing Sheet

Genus and species: *Petunia* x *atkinsiana* (syn. *P.* x *hybrida*).

Variety denomination: 'KLEPH24827'.

BACKGROUND OF THE NEW PLANT

The present invention comprises a new and distinct variety of petunia, botanically known as *Petunia* x *atkinsiana* (syn. *P.* x *hybrida*) and hereinafter referred to by the variety name 'KLEPH24827'. 'KLEPH24827' is a selection from a controlled cross between the proprietary female petunia line 'PH-2013-4523' (unpatented) and the male petunia line 'PH-2019-9782' (unpatented).

In July of 2020, the proprietary female petunia line 'PH-2013-4523' (unpatented) and the proprietary male petunia line 'PH-2019-9782' (unpatented) were cross pollinated in July 2020 in Latina, Italy and seeds were obtained. The seeds were sown and plants were grown for evaluation. A plant line was selected in April 2021 in Latina, Italy and named 'KLEPH24827'. In May 2021, 'KLEPH24827' was first vegetatively propagated by terminal tip cuttings and tissue culture in Latina, Italy. 'KLEPH24827' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Pink-purple flowers with purple veins; and
2. Semi-trailing to trailing plant habit.

DESCRIPTION OF THE PHOTOGRAPH

This new petunia plant is illustrated by the accompanying photograph, which shows a close-up of the flower of the plant. The plant is about 20 weeks old in April 2024, grown outdoors in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEPH24827'. The data which define these characteristics were collected from asexual reproductions carried out in Latina, Italy. Data was collected on thirteen-week-old plants grown indoors in Latina, Italy under greenhouse conditions in May 2025. Color references are to The R.H.S. Colour Chart of The Royal Horticultural Society of London (R.H.S.), 5$^{th}$ edition (2007).

Classification:
- *Family.*—Solanaceae.
- *Species.*—*Petunia* x *atkinsiana* (syn. *P.* x *hybrida*).
- *Common name.*—Petunia.
- *Variety.*—'KLEPH24827'.

Parentage:
- *Female parent.*—'PH-2013-4523' (unpatented).
- *Male parent.*—'PH-2019-9782' (unpatented).

Plant:
- *Form and habit.*—Medium to high vigor, semi-trailing to trailing habit.
- *Height* (*from top of soil*).—16.0 cm.
- *Width* (*horizontal plant diameter*).—65.0 cm.
- *Propagation type.*—Vegetative by terminal tip cuttings and tissue culture.
- *Time to produce a finished flowering plant.*—About 13 weeks in winter under short day conditions, about 7.5 weeks in spring.
- *Time to initiate and develop roots.*—2 to 3 weeks.
- *Root description.*—Moderate density, moderate branching, white roots (RHS 155C).

Stems:
- *Average number* (*basal*).—9.
- *Length of basal branches* (*from the base of the stem to the tip*).—42.0 cm.

*Internode length.*—1.0 cm.
*Diameter of branches (from midpoint).*—0.4 cm.
*Stem color.*—*RHS* 144A.
*Anthocyanin.*—Present, RHS 177A.
*Texture.*—Pubescent.

Leaves:
*Arrangement.*—Alternate along the stem and opposite under the inflorescence.
*Length.*—7.0 cm.
*Width.*—4.0 cm.
*Shape.*—Elliptic tending to circular.
*Apex.*—Obtuse.
*Base.*—Attenuate.
*Margin.*—Entire.
*Immature leaf color.*—Upper surface: RHS 137B. Lower surface: RHS 138B.
*Mature leaf color.*—Upper surface: RHS 137B. Lower surface: RHS 138B.
*Texture.*—Upper surface: Pubescent. Lower surface: Pubescent.
*Venation pattern.*—Arcuate.
*Venation color.*—Upper surface: RHS 138B. Lower surface: RHS 144A.
*Petioles.*—Length: 1.5 cm. Diameter: 0.3 cm. Color: RHS 144B. Texture: Pubescent.

Flower bud:
*Shape.*—Irregularly oblong.
*Length.*—4.0 cm.
*Diameter.*—0.7 cm.
*Color at tight bud.*—RHS 154C.
*Texture.*—Pubescent.

Inflorescence:
*Blooming habit (flowering season).*—Continuously flowering during spring and summertime.
*Inflorescence type.*—Sympodial, with monochasial growth.
*Number of flowers per node.*—1.
*Lastingness of individual blooms on the plant.*—About 10 days.
*Fragrance.*—Absent.
*Flowers.*—Arrangement: Composed of 5 petals, fused at the base. Diameter (flower face): 6.5 cm. Depth (total length of flower): 6.0 cm. Throat/Funnel: Length: 3.5 cm. Diameter (at opening): 1.6 cm. Texture: Inner surface: Smooth. Outer surface: Pubescent. Color: Inner surface: RHS N186A. Outer surface: RHS 157A. Petals: Color, mature flower (fully opened): Upper surface: RHS N74B to RHS N74C with veins close to RHS N78A. Lower surface: RHS 74A to RHS 74D. Apex: Slightly cuspidate. Base: Fused. Shape: Funnelform. Margin: Entire. Strength of waviness: Medium. Degree of lobation: Medium.
*Calyx arrangement.*—5 sepals fused at the base.
*Sepals.*—Color: Upper surface: RHS 137B. Lower surface: RHS 138A. Length: 1.5 cm. Width: 0.4 cm. Shape: Linear. Apex: Acute. Base: Attenuate. Margin: Entire. Texture: Upper surface: Pubescent. Lower surface: Pubescent.
*Pedicels.*—Color: RHS 144A. Length: 2.3 cm. Diameter: 0.15 cm. Texture: Pubescent.

Reproductive organs:
*Stamens.*—Quantity: 5. Shape: Needle with oblong head. Filament: Length: From 1.2 cm to 1.5 cm. Diameter: 0.01 cm. Color: RHS N155A. Anther: Shape: Oblong. Color: RHS 92A. Length: 0.25 cm. Diameter: 0.2 cm. Pollen: Color: RHS 96A. Amount: Sparse.
*Pistils.*—Quantity per flower: 1. Length: 2.5 cm. Stigma color: RHS N137C. Style color: RHS 144D.

Fruit and seed set: None observed.
Disease and pest/insect resistance: None observed.

COMPARISON WITH PARENTAL LINES AND KNOWN VARIETY

'KLEPH24827' is a distinct variety of petunia. 'KLEPH24827' is distinguished from its parents as described in Table 1:

TABLE 1

Comparison with Parental Lines

| Characteristic | Subject Variety 'KLEPH24827' | Female parent 'PH-2013-4523' (unpatented) | Male Parent 'PH-2019-9782' (unpatented) |
|---|---|---|---|
| Flower color | Pink purple with purple veins | White pinkish with dark pink violet veins | Smaller and darker color (compared to 'KLEPH24827' with stronger-colored veins |
| Growth habit | Semi-trailing to trailing | Semi-trailing to semi-upright | Semi-upright |

'KLEPH24827' is most similar to the commercial petunia plant named 'KLEPH14273' (unpatented). Differences between the two varieties are described in Table 2:

TABLE 2

Comparison with Similar Variety

| Characteristic | Subject Variety 'KLEPH24827' | Commercial line 'KLEPH14273' (unpatented) |
|---|---|---|
| Flower | Medium degree of waviness of petals compared to 'KLEPH14273' | Higher degree of waviness of petals and stronger dark veins than 'KLEPH24827' |

I claim:

1. A new and distinct variety of Petunia plant named 'KLEPH24827' as shown and described herein.

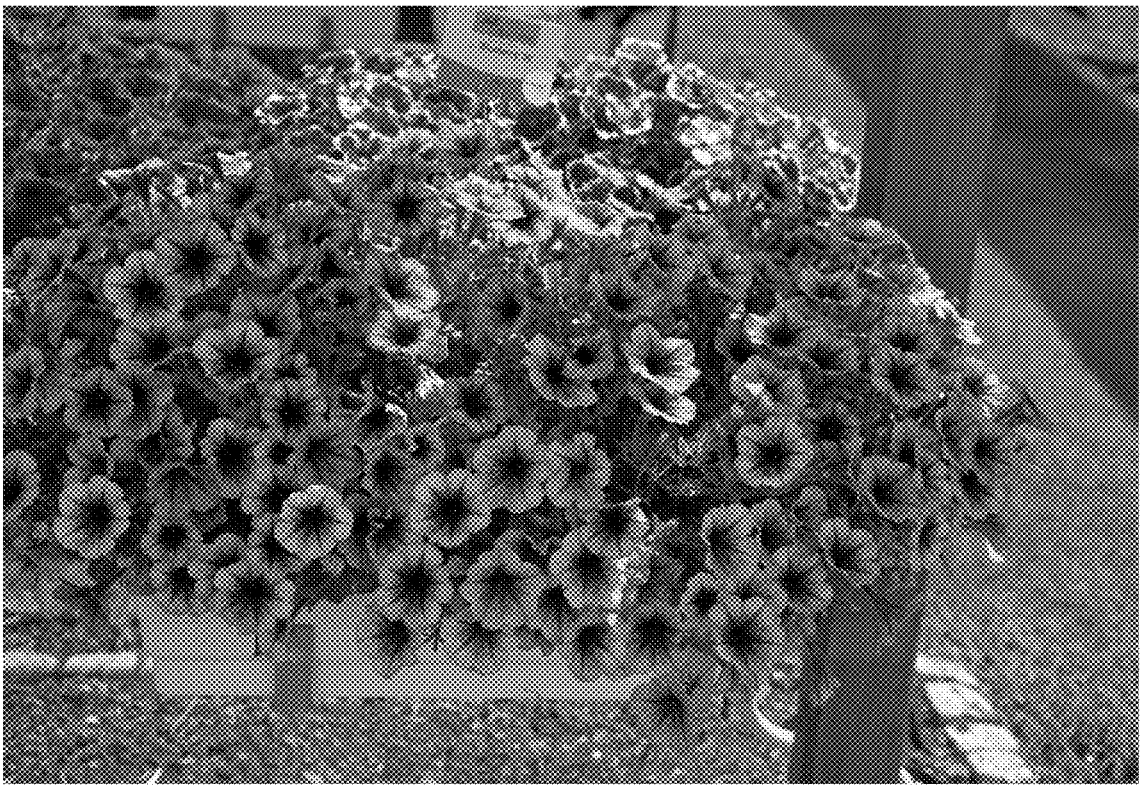

* * * * *